United States Patent
Morin et al.

(10) Patent No.: US 10,871,482 B2
(45) Date of Patent: *Dec. 22, 2020

(54) TARGET DETECTION WITH NANOPORE AND A POLYMER SCAFFOLD COMPLEX

(71) Applicant: Ontera Inc., Santa Cruz, CA (US)

(72) Inventors: Trevor J. Morin, Santa Cruz, CA (US); Daniel Alexander Heller, Santa Cruz, CA (US); William B. Dunbar, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 442 days.

This patent is subject to a terminal disclaimer.

(21) Appl. No.: 15/160,647

(22) Filed: May 20, 2016

(65) Prior Publication Data

US 2016/0266089 A1 Sep. 15, 2016

Related U.S. Application Data (63) Continuation of application No. 14/270,283, filed on May 5, 2014, now abandoned.
(Continued)

(51) Int. Cl.
*G01N 33/545* (2006.01)
*G01N 33/487* (2006.01)
(Continued)

(52) U.S. Cl.
CPC ..... *G01N 33/48721* (2013.01); *C12Q 1/6869* (2013.01); *G01N 27/4473* (2013.01);
(Continued)

(58) Field of Classification Search
CPC .. C12Q 1/6804; C12Q 1/6825; C12Q 1/6869; G01N 33/537; G01N 33/6872; G01N 33/48721; B82Y 15/00
See application file for complete search history.

(56) References Cited

U.S. PATENT DOCUMENTS 5,965,361 A 10/1999 Kigawa et al.
7,947,485 B2 5/2011 Wu et al.
(Continued)

FOREIGN PATENT DOCUMENTS

| CN | 103364445 A | 10/2013 |
|---|---|---|
| CN | 104109633 A | 10/2014 |
| WO | WO-03/044482 A2 | 5/2003 |
| WO | WO 2013012881 A2 | 1/2013 |
| WO | WO 2013/123450 A1 | 8/2013 |
| WO | WO 2018/093976 A1 | 5/2018 |

OTHER PUBLICATIONS

Communication pursuant to Article 94(3) EPC for European Patent Application No. EP 14733761.2, dated Aug. 22, 2017, 3 Pages.
(Continued)

*Primary Examiner* — Christopher L Chin
(74) *Attorney, Agent, or Firm* — Fenwick & West LLP (57) ABSTRACT

Provided are methods for detecting a target molecule or particle suspected to be present in a sample, comprising (a) contacting the sample with (i) a fusion molecule comprising a ligand capable of binding to the target molecule or particle and a binding domain, and (ii) a polymer scaffold comprising at least one binding motif to which the binding domain is capable of binding, under conditions that allow the target molecule or particle to bind to the ligand and the binding domain to bind to the binding motif; (b) loading the polymer into a device comprising a pore that separates an interior space of the device into two volumes, and configuring the device to pass the polymer through the pore from one volume to the other volume, wherein the device further comprises a sensor adjacent to the pore configured to identify objects passing through the pore; and (c) determining, with the sensor, whether the fusion molecule or particle bound to the binding motif is bound to the target molecule or particle, thereby detecting the presence of the target molecule or particle in the sample.

21 Claims, 6 Drawing Sheets

Related U.S. Application Data (60) Provisional application No. 61/820,083, filed on May 6, 2013.

(51) Int. Cl.

| | | |
|---|---|---|
| *G01N 33/543* | (2006.01) | |
| *G01N 33/569* | (2006.01) | |
| *G01N 33/574* | (2006.01) | |
| *C12Q 1/6869* | (2018.01) | |
| *G01N 27/447* | (2006.01) | |
| *G01N 33/53* | (2006.01) | |
| *G01N 33/536* | (2006.01) | |

(52) U.S. Cl.
CPC ... *G01N 27/44791* (2013.01); *G01N 33/5302* (2013.01); *G01N 33/536* (2013.01); *G01N 33/54306* (2013.01); *G01N 33/54366* (2013.01); *G01N 33/56911* (2013.01); *G01N 33/56983* (2013.01); *G01N 33/574* (2013.01)

(56) References Cited

U.S. PATENT DOCUMENTS

| | | | |
|---|---|---|---|
| 8,557,529 B2 | 10/2013 | Polonksy et al. | |
| 9,983,191 B2* | 5/2018 | Morin | C12Q 1/6869 |
| 10,048,245 B2 | 8/2018 | Morin et al. | |
| 2004/0197793 A1* | 10/2004 | Hassibi | C12Q 1/6825 435/6.12 |
| 2004/0224336 A1* | 11/2004 | Wagner | C12Q 1/6837 435/6.11 |
| 2005/0026202 A1 | 2/2005 | Edman et al. | |
| 2008/0050752 A1* | 2/2008 | Sun | G01N 33/48721 435/7.2 |
| 2009/0050492 A1* | 2/2009 | Alocilja | C12Q 1/6825 205/782 |
| 2012/0276530 A1 | 11/2012 | Meller et al. | |
| 2013/0233709 A1 | 9/2013 | Dunbar et al. | |
| 2014/0318962 A1 | 10/2014 | Luan et al. | |
| 2014/0329225 A1 | 11/2014 | Morin | |
| 2014/0378331 A1 | 12/2014 | Morin | |
| 2015/0205710 A1 | 7/2015 | Zhang | |
| 2015/0337366 A1 | 11/2015 | Davis et al. | |
| 2016/0200773 A1 | 7/2016 | Morin | |
| 2016/0245802 A1 | 8/2016 | Morin et al. | |
| 2016/0258939 A1 | 9/2016 | Morin et al. | |
| 2017/0074855 A1 | 3/2017 | Morin et al. | |
| 2017/0234850 A1 | 8/2017 | Morin | |
| 2017/0349940 A1 | 12/2017 | Morin et al. | |
| 2018/0023114 A1 | 1/2018 | Morin et al. | |
| 2018/0023115 A1 | 1/2018 | Morin et al. | |
| 2018/0155768 A1 | 6/2018 | Cohen et al. | |
| 2018/0363035 A1 | 12/2018 | Morin et al. | |
| 2019/0055592 A1 | 2/2019 | Morin et al. | |

OTHER PUBLICATIONS

Communication pursuant to Article 94(3) EPC for European Patent Application No. EP 14747765.7, dated Aug. 23, 2017, 3 Pages.

Office Action for U.S. Appl. No. 15/160,697, dated Oct. 23, 2017, 15 Pages.

Bezrukov S. M. et al: "Counting Polymers Moving Through a Single Ion Channel", Nature, Jul. 28 1994, pp. 279-281, vol. 370, Nature Publishing Group, United Kingdom.

Kasianowicz J. et al: "Simultaneous Multianalyte Detection with a Nanometer-Scale Pore", Analytical Chemistry, May 15, 2001, pp. 2268-2272, vol. 73(10).

Niemeyer C M: "The developments of semisynthetic DNA-protein conjugates", Trends in Biotechnology, Sep. 2002, pp. 395-401, vol. 20(9), Elsevier Publications, Cambridge, GB.

Wanunu M. et al: "DNA Profiling Using Solid-State Nanopores: Detection of DNA-Binding Molecules", NANO Letters, Oct. 14, 2009, pp. 3498-3502, vol. 9 (10).

Winters-Hilt S. "Nanopore Detector based analysis of single-molecule conformational kinetics and binding interactions", Sep. 26, 2006, pp. 1-27, vol. 7(2), BMC Bioinformatics, Biomed Central, London, GB.

International Search Report and Written Opinion for International Application No. PCT/US2014/036861, dated Sep. 18, 2014, 12 pages.

PCT Written Opinion of the International Preliminary Examining Authority for PCT/US2014/036861, dated Apr. 15, 2015, 7 Pages.

PCT International Search Report and Written Opinion for PCT/US2014/046397, dated Feb. 2, 2015, 11 Pages.

International Preliminary Report on Patentability for PCT/US2014/036861, dated Sep. 2, 2015, 8 Pages.

Office Action for U.S. Appl. No. 14/270,283, Dec. 11, 2015, 6 Pages.

Communication pursuant to Article 94(3) EPC for European Patent Application No. EP 14733761.2, dated Jan. 17, 2017, 3 Pages.

Office Action for U.S. Appl. No. 15/160,697, dated Jan. 11, 2017, 32 Pages.

Haque, et al., "Solid-State and Biological Nanopore for Real-Time Sensing of Single Chemical and Sequencing of DNA," Nano Today, 2013, 8, pp. 56-74.

Howorka, et al., "Nanopore Analytics: Sensing of Single Molecules," Chem. Soc. Rev., 2009, 38, pp. 2360-2384.

Miles, et al., "Single Molecule Sensing With Solid-State Nanopores: Novel Materials, Methods, and Applications," Chem Soc Rev, 2013, 42(15), pp. 1-15.

Reiner, et al., "Disease Detection and Management Via Single Nanopore-Based Sensors," Chemical Reviews, 2012, 112, pp. 6431-6451.

Singer, et al., "Nanopore Based Sequence Specific Detection of Duplex DNA for Genomic Profiling," Nano Lett., 2010, 10, pp. 738-742.

Japan Patent Office, Office Action, Japanese Patent Application No. 2017-511140, dated Mar. 26, 2018, 7 pages.

Kowalczyk, S.W. et al., "Detection of Local Protein Structures along DNA Using Solid-State Nanopores," Nano Letters, 2010, vol. 10, pp. 324-328.

United States Office Action, U.S. Appl. No. 15/160,697, dated Jan. 11, 2019, 28 pages.

United States Office Action, U.S. Appl. No. 15/160,697, dated May 8, 2018, 16 pages.

United States Office Action, U.S. Appl. No. 14/991,851, dated Jun. 11, 2018, 20 pages.

\* cited by examiner

TARGET DETECTION WITH NANOPORE AND A POLYMER SCAFFOLD COMPLEX

CROSS-REFERENCE TO RELATED APPLICATIONS

This application is a continuation of U.S. application Ser. No. 14/270,283, filed May 5, 2014, which claims the benefit to U.S. provisional application Ser. No. 61/820,083, filed May 6, 2013, the contents of which are each herein incorporated by reference in their entirety.

BACKGROUND

Detection of nano-scale particles, such as circulating tumor cells, bacteria and viruses, has immersive clinical utility. Currently available methods include immunohistochemistry and nucleic acid-based detection, and cell proliferation is typically required before a sensitive detection can be carried out.

Molecular detection and quantitation are also important, and can be carried out with various methods depending on the type of the molecule. For instance, nucleotide sequences can be detected by virtue of their sequence complementarity to a probe or primer, through hybridization and/or amplification, or in fewer occasions with a protein that recognize the sequence. A protein, on the other hand, is commonly detected with an antibody that specifically recognizes and binds the protein. An enzyme-linked immuno sorbent assay (ELISA), in this respect, is highly commercialized and commonly used.

Methods also exist for detecting or quantitating various other large or small molecules, such as carbohydrates, chemical compounds, ions, and elements.

Methods and systems for highly sensitive detection of molecules as well as particles, such as tumor cells and pathogenic organisms, have broad applications, in particular clinically, for pathogen detection and disease diagnosis, for instance.

SUMMARY

In one embodiment, the present disclosure provides a method for assaying whether a target molecule or particle is present in a sample, comprising: (a) contacting the sample with (i) a fusion molecule comprising a ligand capable of binding to the target molecule or particle and a binding domain, and (ii) a polymer scaffold comprising at least one binding motif to which the binding domain of the fusion molecule is capable of binding, under conditions that allow the target molecule or particle to bind to the ligand and the binding domain to bind to the binding motif; (b) loading the polymer into a device comprising a pore that separates an interior space of the device into two volumes, and configuring the device to pass the polymer through the pore from one volume to the other volume, wherein the device further comprises a sensor adjacent to the pore configured to identify objects passing through the pore; and (c) determining, with the sensor, whether the fusion molecule bound to the binding motif is bound to the target molecule or particle, thereby detecting the presence of the target molecule or particle in the sample.

In some aspects, the target molecule is selected from the group consisting of a protein, a peptide, a nucleic acid, a chemical compound, an ion, and an element.

In some aspects, the target particle is selected from the group consisting of protein complexes and protein aggregates, protein/nucleic acid complexes, fragmented or fully assembled viruses, bacteria, cells, and cellular aggregates.

In some aspects, step (a) of the method for assaying whether a target molecule or particle is present in a sample is performed prior to step (b). In some aspects, step (b) is performed prior to step (a).

In some aspects, the method further comprises applying a condition suspected to alter the binding between the target molecule or particle and the ligand and carrying out the determination again. In some aspects, the condition is selected from the group consisting of removing the target molecule or particle from the sample, adding an agent that competes with the target molecule or particle or the ligand for binding, and changing the pH, salt, or temperature.

In some aspects, the binding motif comprises a chemical modification for binding to the binding domain. In some aspects, the chemical modification is selected from the group consisting of acetylation, methylation, summolation, glycosylation, phosphorylation, and oxidation.

In some aspects, the polymer comprises a deoxyribonucleic acid (DNA), a ribonucleic acid (RNA), a peptide nucleic acid (PNA), a DNA/RNA hybrid, or a polypeptide.

In some aspects, the binding domain is selected from the group consisting of a helix-turn-helix, a zinc finger, a leucine zipper, a winged helix, a winged helix turn helix, a helix-loop-helix and an HMG-box.

In some aspects, the binding domain is selected from the group consisting of locked nucleic acids (LNAs), PNAs, transcription activator-like effector nucleases (TALENs), clustered regularly interspaced short palindromic repeats (CRISPRs), and aptamers.

In some aspects, the ligand is a protein. In some aspects, the ligand is selected from the group consisting of an antibody, an epitope, a hormone, a neurotransmitter, a cytokine, a growth factor, a cell recognition molecule, and a receptor.

In some aspects, the binding domain and the ligand are linked, via a covalent bond, a hydrogen bond, an ionic bond, a metallic bond, van der Walls force, hydrophobic interaction, or planar stacking interaction, or are translated as a continuous polypeptide, to form the fusion molecule.

In some aspects, the method further comprises contacting the sample with a detectable label capable of binding to the target molecule or particle or target/ligand complex.

In some aspects, the polymer comprises at least two units of the binding motif.

In some aspects, the polymer comprises at least two different binding motifs: the sample is in contact with at least two fusion molecules each comprising a different binding domain capable of binding to each binding motif and a different ligand capable of binding to a different target molecule or particle; and the sensor is configured to identify whether the fusion molecule bound to each binding motif is bound to a target molecule or particle.

In some aspects, the device comprises electrodes to apply a voltage differential between the two volumes.

In some aspects, the device comprises an upper chamber, a middle chamber and a lower chamber, wherein the upper chamber is in communication with the middle chamber through a first pore, and the middle chamber is in communication with the lower chamber through a second pore.

In one aspect, the first pore and second pore are about 1 nm to about 100 nm in diameter. Such pores can be suitable for detecting molecules such as proteins and nucleic acids. In one aspect, the first pore and second pore are as large as about 50,000 nm in diameter, which can be suitable for detecting larger particles such as tumor and bacterial cells.

In some aspects, the pores are about 10 nm to about 1000 nm apart from each other.

In some aspects, each of the chambers comprises an electrode for connecting to a power supply.

In some aspects, the method further comprises moving the polymer at a reversed direction after the binding motif passes through the pore, such as to identify, again, whether the fusion molecule bound to each binding motif is bound to a target molecule or particle.

Also provided are kits, packages or mixtures for detecting the presence of a target molecule or particle. In some aspects, the kit, package or mixture comprises (a) a fusion molecule comprising a ligand capable of binding to the target molecule or particle and a binding domain, (b) a polymer scaffold comprising at least one binding motif to which the binding domain is capable of binding, (c) a device comprising a pore that separates an interior space of the device into two volumes, wherein the device is configured to allow the polymer to pass through the pore from one volume to the other volume, and wherein the device further comprises a sensor adjacent to the pore configured to identify whether the binding motif is (i) bound to the fusion molecule while the ligand is bound to the target molecule or particle, (ii) bound to the fusion molecule while the ligand is not bound to the target molecule or particle, or (iii) not bound to the fusion molecule.

In some aspects, the kit, package or mixture further comprises a sample suspected of containing the target molecule or particle. In some aspects, the sample further comprises a detectable label capable of binding to the target molecule or particle or the ligand/target molecule or particle complex.

BRIEF DESCRIPTION OF THE DRAWINGS

Provided as embodiments of this disclosure are drawings which illustrate by exemplification only, and not limitation, wherein:

FIG. 5A, FIG. 5B, and FIG. 5C illustrate a nanopore device with at least two pores separating multiple chambers.

Specifically.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present nutrients, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a", "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary, and that equivalents of such are known in the art.

Molecular Detection

The present disclosure provides methods and systems for molecular detection and quantitation. In addition, the methods and systems can also be configured to measure the affinity of a molecule binding with another molecule. Further, such detection, quantitation, and measurement can be carried out in a multiplexed manner, greatly increasing its efficiency.

Figure 1:
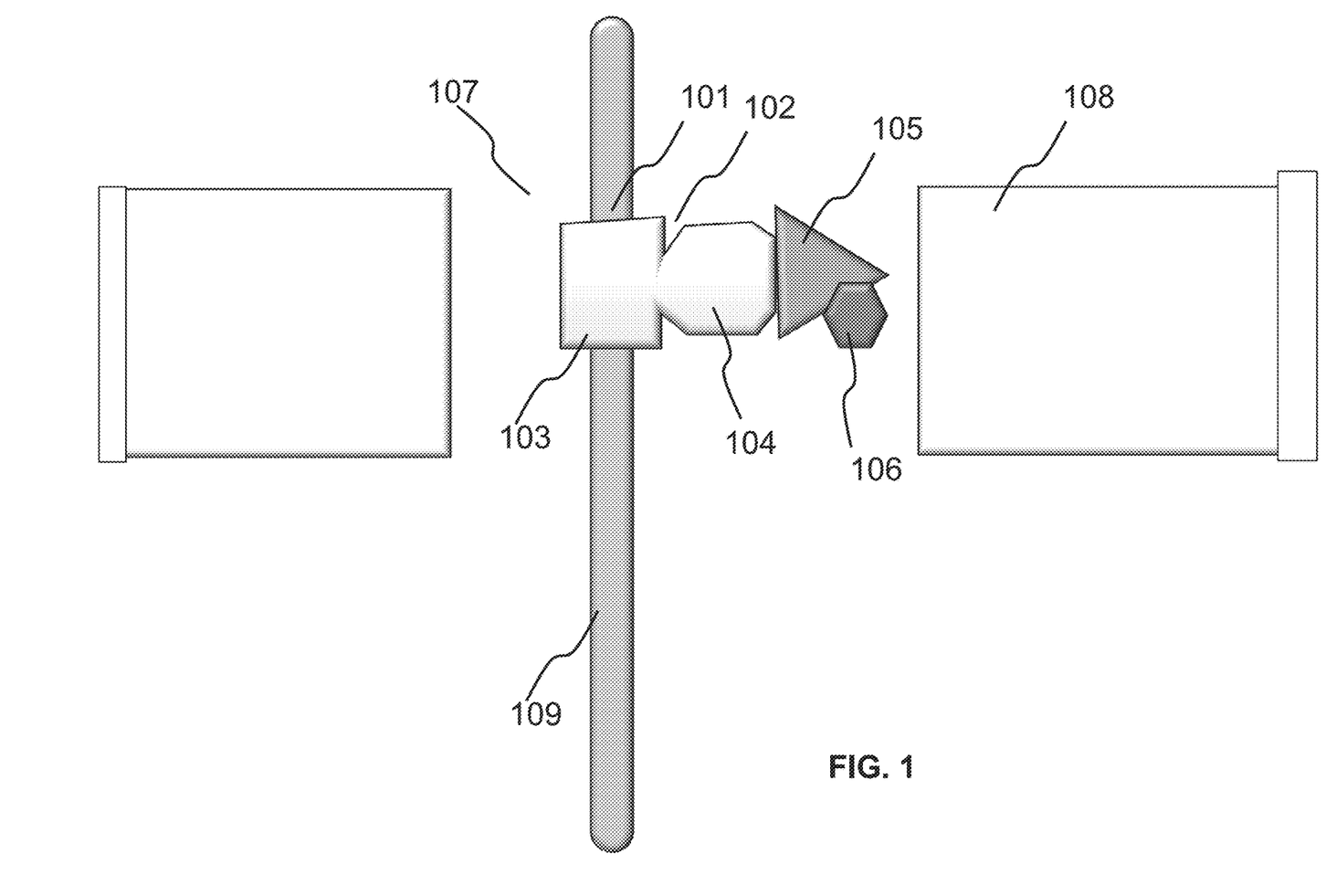
FIG. 1 illustrates the detection of a target molecule or particle with one embodiment of the presently disclosed method.

FIG. 1 provides an illustration of one embodiment of the disclosed methods and systems. More specifically, the system includes a ligand 104 that is capable of binding to a target molecule 105 to be detected or quantitated. The ligand 104 can be part of, or be linked to, a binding moiety (referred to as "binding domain") 103 that is capable of binding to a specific binding motif 101 on a polymer scaffold 109. Together, the ligand 104 and the binding domain 103 form a fusion molecule 102.

Therefore, if all present in a solution, the fusion molecule 102 binds, on one end, to a polymer scaffold 109 (or simply "polymer") through the specific recognition and binding between the binding motif 101 and the binding domain 103, and on the other end, to the target molecule 105 by virtue of the interaction between the ligand 104 and the target molecule 105. Such bindings cause the formation of a complex that includes the polymer 109, the fusion molecule 102 and the target molecule 105.

The formed complex can be detected by a device 108 that includes a pore 107 that separates an interior space of the device into two volumes, and a sensor adjacent to the pore 107 configured to identify objects passing through the pore 107. This device is referred throughout as a "nanopore". In some embodiments, the nanopore 108 also includes means, such as electrodes connected to power sources, for moving the polymer 109 from one volume to another, across the pore 107. As the polymer 109 can be charged or be modified to contain charges, one example of such means generates a potential or voltage differential across the pore 107 to facilitate and control the movement of the polymer 109.

When a sample that includes the formed complex is loaded to the nanopore 108, the nanopore 108 can be configured to pass the polymer 109 through the pore 107. When the binding motif 101 is within the pore or adjacent to the pore 107, the binding status of the motif 101 can be detected by the sensor.

The "binding status" of a binding motif, as used herein, refers to whether the binding motif is bound to a fusion molecule with a corresponding binding domain, and whether the fusion molecule is also bound to a target molecule. Essentially, the binding status can be one of three potential statuses: (i) the binding motif is free and not bound to a fusion molecule (see 305 in FIG. 3); (ii) the binding motif is bound to a fusion molecule that does not bind to a target molecule (see 306 in FIG. 3); or (iii) the binding motif is bound to a fusion molecule that is bound to a target molecule (see 307 in FIG. 3).

Figure 3:
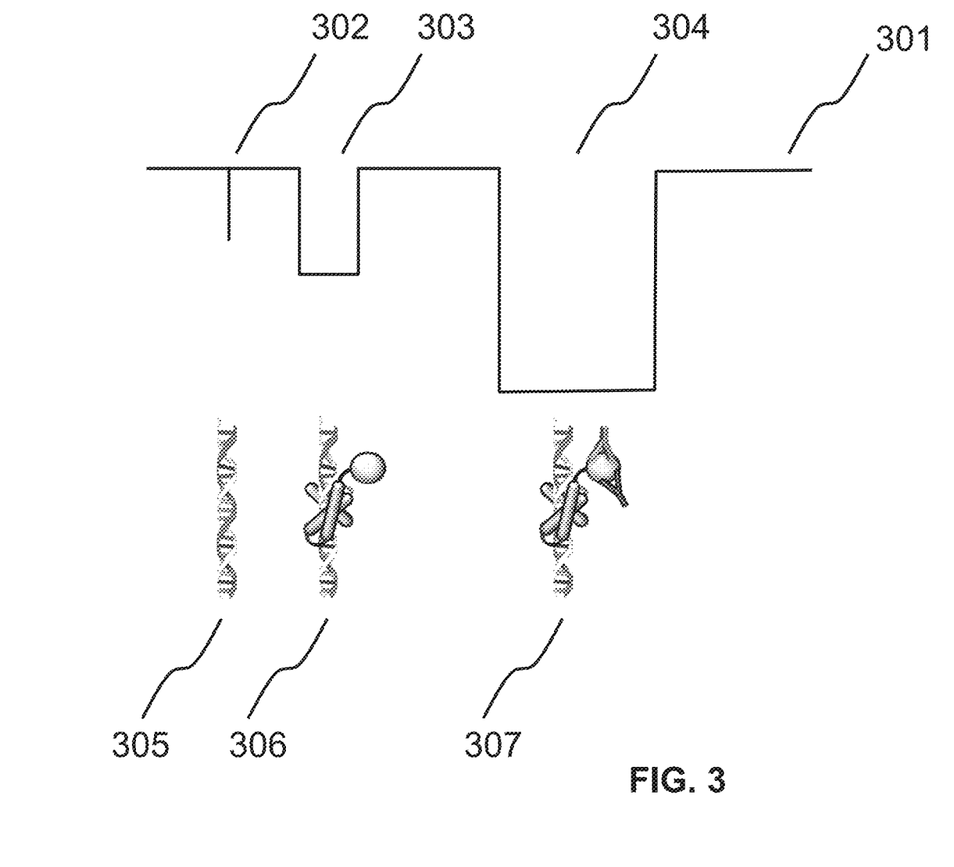
FIG. 3 shows that a binding between a target molecule or particle and a fusion molecule can be detected since it has a different current profile compared to the fusion molecule alone or the DNA alone, when passing through a nanopore.

Detection of the binding status of a binding motif can be carried out by various methods. In one aspect, by virtue of the different sizes of the binding motif at each status, when the binding motif passes through the pore, the different sizes result in different electrical currents across the pore. In one aspect as shown in FIG. 3, the measured current signals 301, when 305, 306, and 307 pass through the pore, are signals 302, 303, and 304, respectively. In this respect, no separate sensor is required for the detection, as the electrodes, which are connected to power sources and can detect the current, can serve the sensing function. Either one or both of the electrodes, therefore, serve as a "sensor."

In some aspects, an agent 106 as shown in FIG. 1 is added to the complex to aid detection. This agent is capable to bind to the target molecule or the ligand/target molecule complex. In one aspect, the agent includes a charge, either negative or positive, to facilitate detection. In another aspect, the agent adds size to facilitate detection. In another aspect, the agent includes a detectable label, such as a fluorophore.

In this context, an identification of status (iii) indicates that a polymer-fusion molecule-target molecule complex has formed. In other words, the target molecule is detected.

Particle Detection

The present disclosure also provides, in some aspects, methods and systems for detecting, quantitating, and measuring particles such as cells and microorganisms, including viruses, bacteria, and cellular aggregates.

In some aspects, the pore that separates the device into two volumes has a size that allows particles, such as viruses, bacteria, cells, or cellular aggregates, to pass through. A ligand that is capable of binding to a target particle to be detected or quantitated can be included in the solution in the device such that the ligand can bind to the unique target particle and the polymer scaffold through a binding domain and a binding motif to form a complex. Many such particles have unique markers on their surfaces which can be specifically recognized by a ligand. For instance, tumor cells can have tumor antigens expressed on the cell surface, and bacterial cells can have endotoxins attached on the cell membrane.

When the formed complex in a solution loaded into the nanopore device is moved along with the polymer scaffold to pass through the pore, the binding status of the complex within or adjacent to the pore can be detected such that the target microorganisms bound to the ligands can be identified using methods similar to the molecular detection methods described elsewhere in the disclosure.

Polymer Scaffold

A polymer scaffold suitable for use in the present technology is a linear or linearized molecule, which has a length that is several magnitudes greater than its width. Such a scaffold can be loaded into a nanopore device and pass through the pore from one end to the other.

Non-limiting examples of polymers include nuclei acids, such as deoxyribonucleic acid (DNA), ribonucleic acid (RNA), or peptide nucleic acid (PNA), and linearized proteins or peptides. In some aspects, the DNA or RNA can be single-stranded or double-stranded, or can be a DNA/RNA hybrid molecule.

In one aspect, the polymer is synthetic or chemically modified. Chemical modification can help to stabilize the polymer, add charges to the polymer to increase mobility, maintain linearity, or add or modify the binding specificity. In some aspects, the chemical modification is acetylation, methylation, summolation, oxidation, phosphorylation, or glycosylation.

In some aspects, the polymer is electrically charged. DNA, RNA, PNA and proteins are typically charged under physiological conditions. Such polymers can be further modified to increase or decrease the carried charge. Other polymers can be modified to introduce charges. Charges on the polymer can be useful for driving the polymer to pass through the pore of a nanopore device. For instance, a charged polymer can move across the pore by virtue of an application of voltage across the pore.

In some aspects, when charges are introduced to the polymer, the charges can be added at the ends of the polymer. In some aspects, the charges are spread over the polymer.

In one embodiment, each unit of the charged polymer is charged at the pH selected. In another embodiment, the charged polymer includes sufficient charged units to be pulled into and through the pore by electrostatic forces. For example, a peptide containing sufficient entities which can be charged at a selected pH (lysine, aspartic acid, glutamic acid, etc.) so as to be used in the devices and methods described herein is a charged polymer for purposes of this invention. Likewise, a co-polymer comprising methacrylic acid and ethylene is a charged polymer for the purposes of this invention if there is sufficient charged carboxylate groups of the methacrylic acid residue to be used in the devices and methods described herein. In one embodiment, the charged polymer includes one or more charged units at or close to one terminus of the polymer. In another embodiment, the charged polymer includes one or more charged units at or close to both termini of the polymer. One co-polymer example is a DNA wrapped around protein (e.g.

DNA/nucleosome). Another example of a co-polymer is a linearized protein conjugated to DNA at the N- and C-terminus.

Binding Motifs and Binding Domains

For nucleic acids and polypeptides such as the polymer scaffold, a binding motif can be a nucleotide or peptide sequence that is recognizable by a binding domain, which is typically a functional portion of a protein, although a binding domain does not have to be a peptide. For nucleic acids, for instance, there are proteins that specifically recognize and bind to sequences (motifs) such as promoters, enhancers, thymine-thymine dimers, and certain secondary structures such as bent nucleotide and sequences with single-strand breakage.

In some aspects, the binding motif includes a chemical modification that causes or facilitates recognition and binding by a binding domain. For example, methylated DNA sequences can be recognized by transcription factors, DNA methyltransferases or methylation repair enzymes.

Molecules, in particular proteins, that are capable of specifically recognizing nucleotide binding motifs are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences.

In some aspects, the binding domains can be locked nucleic acids (LNAs), PNAs, transcription activator-like effector nucleases (TALENs), clustered regularly interspaced short palindromic repeats (CRISPRs), or aptamers.

Target Molecule/Particles and Ligands

In the present technology, a target molecule or particle is detected or quantitated by virtue of its binding to a ligand in a fusion molecule that binds to a polymer scaffold. A target molecule or particle and a corresponding binding ligand can recognize and bind each other. For a particle, there can be surface molecules or markers suitable for a ligand to bind (therefore the marker and the ligand form a binding pair).

Examples of binding pairs that enable binding between a target molecule or a molecule on a particle include, but are not limited to, antigen/antibody (or antibody fragment); hormone, neurotransmitter, cytokine, growth factor or cell recognition molecule/receptor; and ion or element/chelate agent or ion binding protein, such as a calmodulin. The binding pairs can also be single-stranded nucleic acids having complementary sequences, enzymes and substrates, members of protein complex that bind each other, enzymes and cofactors, nucleic acid/protein.

Therefore, any target molecule in need of detection or quantitation, such as proteins, peptides, nucleic acids, chemical compounds, ions, and elements, can find a corresponding binding ligand. For the majority of proteins and nucleic acids, an antibody or a complementary sequence can be readily prepared.

Likewise, binding ligands (such as antibodies) can be readily found or prepared for particles, such as protein complexes and protein aggregates, protein/nucleic acid complexes, fragmented or fully assembled viruses, bacteria, cells, and cellular aggregates.

Fusion Molecule

A "fusion molecule" is intended to mean a molecule or complex that contains two functional regions, a binding domain and a ligand. The binding domain is capable of binding to a binding motif on a polymer scaffold, and the ligand is capable of binding to a target molecule.

In some aspects, the fusion molecule is prepared by linking the two regions with a bond or force. Such a bond and force can be, for instance, a covalent bond, a hydrogen bond, an ionic bond, a metallic bond, van der Walls force, hydrophobic interaction, or planar stacking interaction.

In some aspects, the fusion molecule, such as a fusion protein, can be expressed as a single molecule from a recombinant coding nucleotide. In some aspects, the fusion molecule is a natural molecule having a binding domain and a ligand suitable for use in the present technology.

Figure 2:
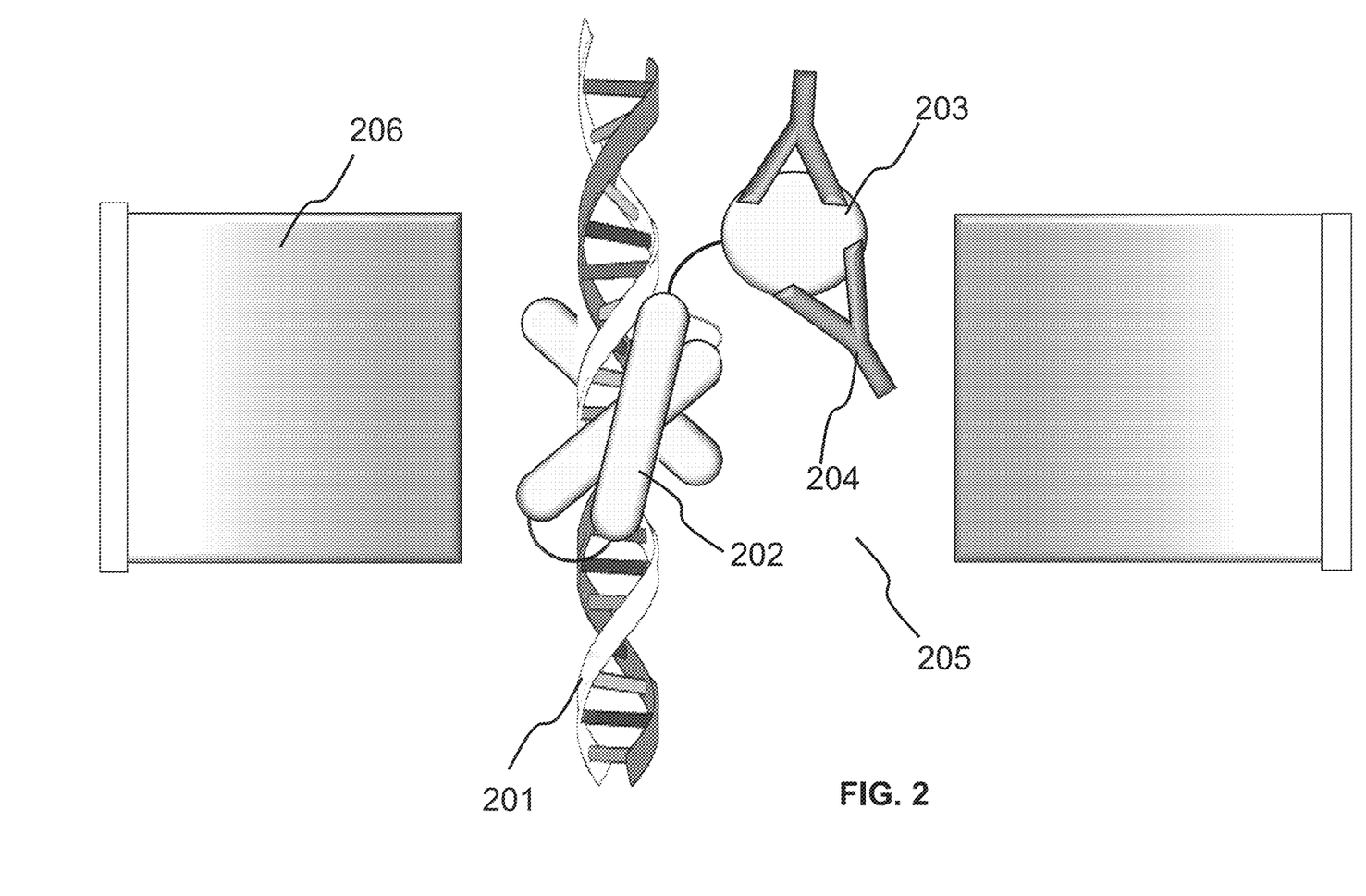
FIG. 2 provides the illustration of a more specific example in which a double-stranded DNA is used as the polymer scaffold and a human immunodeficiency virus (HIV) envelop protein as the ligand, for the detection of an anti-HIV antibody.

FIG. 2 illustrates a more specific embodiment of the system shown in FIG. 1. In FIG. 2, the fusion molecule is a chimeric protein that includes a zinc finger protein or domain 202 and a human immunodeficiency virus (HIV) envelop protein 203. The zinc finger protein 202 can bind to a suitable nucleotide sequence on the polymer scaffold, a double-stranded DNA 201; the HIV envelop protein 203 can bind to an anti-HIV antibody 204 which can be present in a biological sample (e.g., a blood sample from a patient) for detection.

When the double-stranded DNA 201 passes through a pore 205 of a nanopore device 206, the nanopore device 206 can detect whether a fusion molecule is bound to the DNA 201 and whether the bound fusion molecule binds to an anti-HIV antibody 204.

Measurement of Affinity of Binding

The present technology can be used also for measuring the binding affinity between two molecules and to determine other binding dynamics. For instance, after the binding motif passes through the pore of a nanopore device, the device can be reconfigured to reverse the moving direction of the polymer scaffold (as described below) such that the binding motif can pass through the pore again.

Before the binding motif enters the pore again, one can change the conditions in the sample that is loaded into the nanopore device. For instance, the condition can be one or more of removing the target molecule from the sample, adding an agent that competes with the target molecule or the ligand for binding, and changing the pH, salt, or temperature.

Under the changed conditions, the binding motif passes through the pore again. Therefore, whether the target molecule is still bound to the fusion molecule can be detected to determine how the changed conditions impact the binding.

In some aspects, once the binding motif is in the pore, it is retained there while the conditions are changed, and thus the impact of the changed conditions can be measured in situ.

Alternatively or in addition, the polymer scaffold can include multiple binding motifs and each of the binding motifs can bind to a fusion molecule which can bind to a target molecule or particle. While each binding motif passes through the pore, the conditions of the sample can be changed, allowing detection of changed binding between the ligand and the target molecule or particle on a continued basis.

Multiplexing

In some aspects, rather than including multiple binding motif of the same kind as described above, a polymer scaffold can include multiple types of binding motif, each can have different corresponding binding domains. Meanwhile, a sample can include multiple types of fusion molecules, each including one of such binding domains and a ligand for a different target molecule or a target microorganism.

Figure 4:
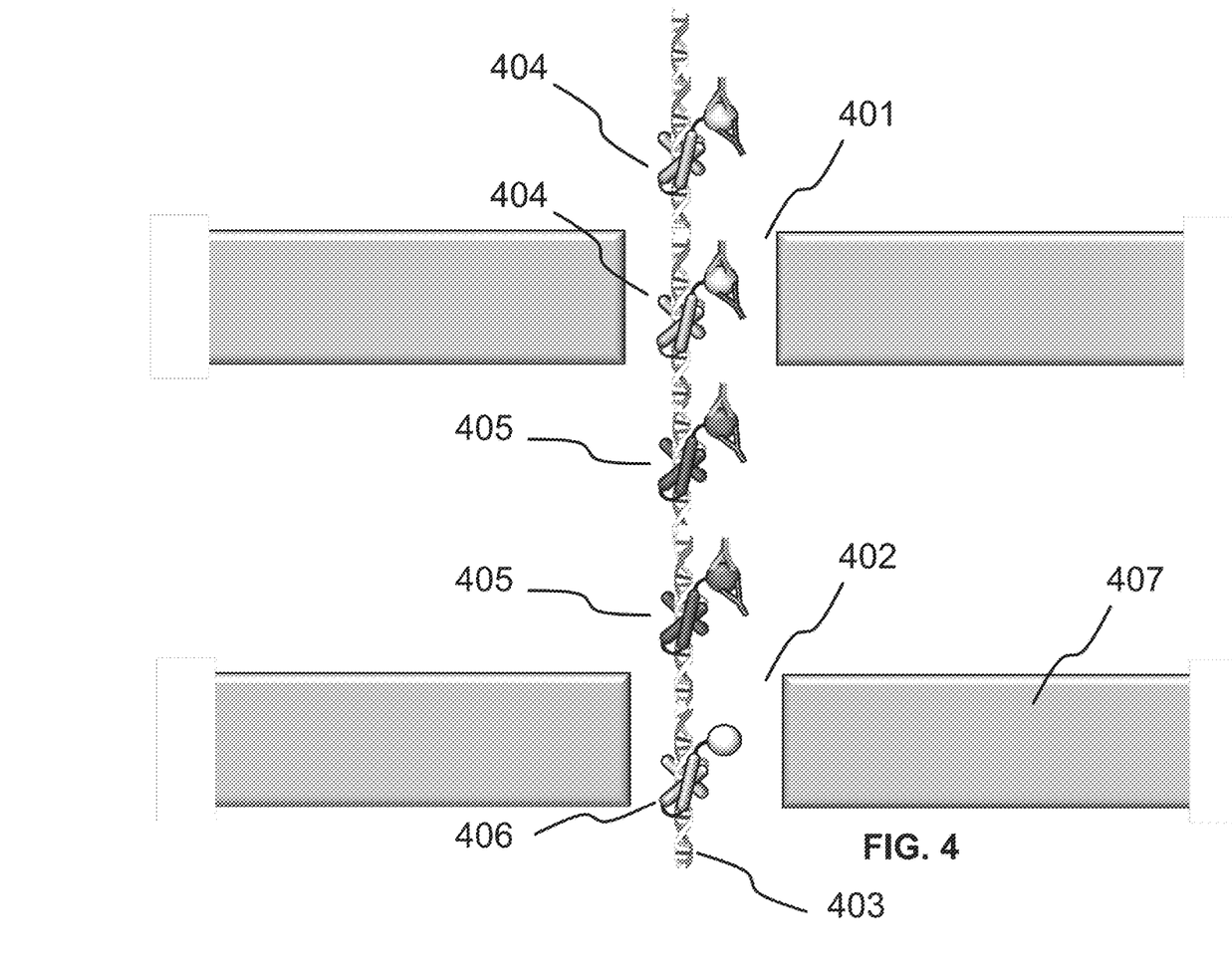
FIG. 4 illustrates the multiplexing capability of the present technology by including different binding motifs in the polymer scaffold.

With such a setting, a single polymer scaffold can be used to detect multiple types of target molecules or target microorganisms. FIG. 4 illustrates such a method. Here, a double-stranded DNA 403 is used as the polymer scaffold, the double-stranded DNA 403 including multiple binding motifs: two copies of 404, two copies of 405, and one copy of 406.

When the DNA passes through a nanopore device 407 that has two coaxial pores, 401 and 402, the binding status of each of the binding motifs is detected, in which both copies of binding motif 404 bind to a corresponding target molecule, both copies of binding motif 405 bind to a corresponding target molecule; and the fusion molecule bound to binding motif 406 does not bind to a corresponding target molecule.

This way, with a single polymer and a single nanopore device, the present technology can detect different target molecules or target microorganisms. Further, by determining how many copies of binding motifs are bound to the target molecules or target microorganisms, and by tuning conditions that impact the bindings, the system can obtain more detailed binding dynamic information.

Nanopore Devices

A nanopore device, as provided, includes at least a pore that separates an interior space of the device into two volumes, and at least a sensor adjacent to the pore configured to identify objects passing through the pore.

The pore(s) in the nanopore device are of a nano scale. In one aspect, each pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In some aspects, each pore is at least about 100 nm, 200 nm, 500 nm, 1000 nm, 2000 nm, 3000 nm, 5000 nm, 10000 nm, 20000 nm, or 30000 nm in diameter. In one aspect, the pore is no more than about 100000 nm in diameter. Alternatively, the pore is no more than about 50000 nm, 40000 nm, 30000 nm, 20000 nm, 10000 nm, 9000 nm, 8000 nm, 7000 nm, 6000 nm, 5000 nm, 4000 nm, 3000 nm, 2000 nm, or 1000 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore(s) in the nanopore device are of a larger scale for detecting large microorganisms or cells. In one aspect, each pore has a size that allows a large cell or microorganism to pass. In one aspect, each pore is at least about 100 nm in diameter. Alternatively, each pore is at least about 200 nm, 300 nm, 400 nm, 500 nm, 600 nm, 600 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, or 5000 nm in diameter.

In one aspect, the pore is no more than about 10000 nm in diameter. Alternatively, the pore is no more than about 9500 nm, 9000 nm, 8500 nm, 8000 nm, 7500 nm, 6000 nm, 6500 nm, 6000 nm, 5500 nm, 5000 nm, 4500 nm, 4000 nm, 3500 nm, 3000 nm, 2500 nm, 2000 nm, 1500 nm, or 1000 nm in diameter.

In one aspect, the pore has a diameter that is between about 100 nm and about 10000 nm, or alternatively between about 200 nm and about 9000 nm, or between about 300 nm and about 8000 nm, or between about 400 nm and about 7000 nm, or between about 500 nm and about 6000 nm, or between about 1000 nm and about 5000 nm, or between about 1500 nm and about 3000 nm.

In some aspects, the nanopore device further includes means to move a polymer scaffold to across the pore and/or means to identify objects that pass through the pore. Further details are provided below, when described in the context of a two-pore device.

Compared to a single-pore nanopore device, a two-pore device can be more easily configured to provide good control of speed and direction of the movement of the polymer across the pores.

In one embodiment, the nanopore device includes a plurality of chambers, each chamber in communication with an adjacent chamber through at least one pore. Among these pores, two pores, namely a first and a second pores, are placed so as to allow at least a portion of a polymer to move out of the first pore and into the second pore. Further, the device includes a sensor capable of identifying the polymer during the movement. In one aspect, the identification entails identifying individual components of the polymer. Preferably, when a single sensor is employed, the single sensor does not include two electrodes placed at both ends of a pore to measure an ionic current across the pore.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymers to move from one chamber to the next simultaneously. Such a multi-pore design can enhance throughput of polymer analysis in the device.

In some aspects, the device further includes means to move a polymer from one chamber to another. In one aspect, the movement results in loading the polymer across both the first pore and the second pore at the same time. In another aspect, the means further enables the movement of the polymer, through both pores, in the same direction.

For instance, in a three-chamber two-pore device (a "two-pore" device), each of the chambers can contain an electrode for connecting to a power supply so that a separate voltage can be applied across each of the pores between the chambers.

In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore.

Figure 5A:
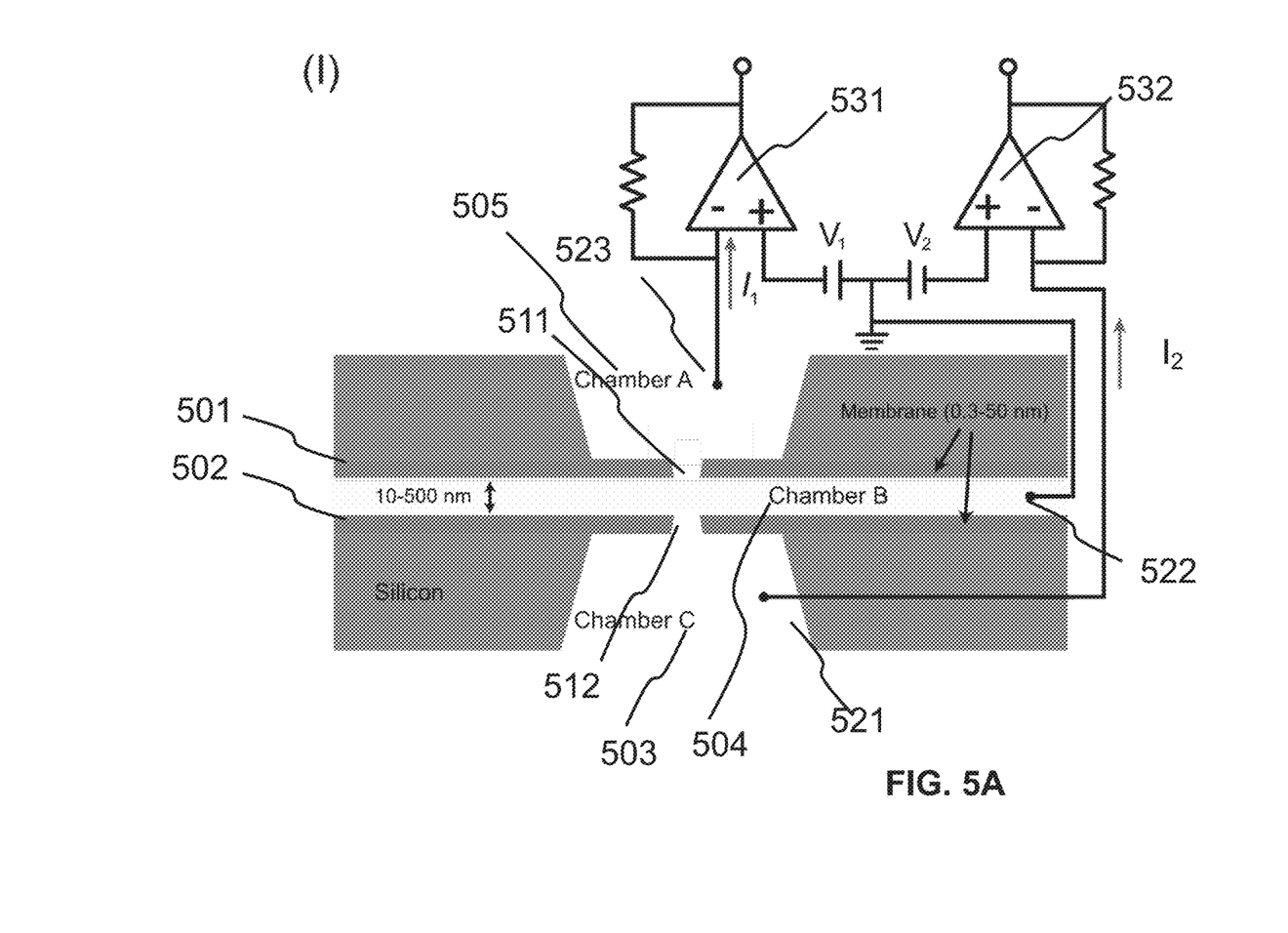
FIG. 5A is a schematic of a dual-pore chip and a dual-amplifier electronics configuration for independent voltage control ($V_1$ or $V_2$) and current measurement ($I_1$ or $I_2$) of each pore. Three chambers, A-C, are shown and are volumetrically separated except by common pores.

In some embodiments as shown in FIG. 5A, the device includes an upper chamber 505 (Chamber A), a middle chamber 504 (Chamber B), and a lower chamber 503 (Chamber C). The chambers are separated by two separating layers or membranes (501 and 502) each having a separate pore (511 or 512). Further, each chamber contains an electrode (521, 522 or 523) for connecting to a power supply.

The annotation of upper, middle and lower chamber is in relative terms and does not indicate that, for instance, the upper chamber is placed above the middle or lower chamber relative to the ground, or vice versa.

Each of the pores 511 and 512 independently has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 70 nm, 60 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore has a substantially round shape. "Substantially round", as used here, refers to a shape that is at least about 80 or 90% in the form of a cylinder. In some embodiments, the pore is square, rectangular, triangular, oval, or hexangular in shape.

Each of the pores 511 and 512 independently has a depth. In one aspect, each pore has a depth that is least about 0.3 nm. Alternatively, each pore has a depth that is at least about 0.6 nm, 1 nm, 2 nm, 3 nm, 4 nm, 5 nm, 7 nm, 6 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm.

In one aspect, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm.

In one aspect, the pore has a depth that is between about 1 nm and about 100 nm, or alternatively, between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In one aspect, the pores are spaced apart at a distance that is between about 10 nm and about 1000 nm. In one aspect, the distance is at least about 10 nm, or alternatively, at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm.

In yet another aspect, the distance between the pores is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no direct blockage between them. Still, in one aspect, the pores are substantially coaxial, as illustrated in FIG. 5A.

In one aspect, as shown in FIG. 5A, the device, through the electrodes 521, 522, and 523 in the chambers 503, 504, and 505, respectively, is connected to one or more power supplies. In some aspects, the power supply includes a voltage-clamp or a patch-clamp for supplying a voltage across each pore, which can also measure the current through each pore independently. In this respect, the power supply and the electrode configuration can set the middle chamber to a common ground for both power supplies. In one aspect, the power supplies are configured to apply a first voltage V1 between the upper chamber 505 (Chamber A) and the middle chamber 504 (Chamber B), and a second voltage V2 between the middle chamber 504 and the lower chamber 503 (Chamber C).

In some aspects, the first voltage $V_1$ and the second voltage $V_2$ are independently adjustable. In one aspect, the middle chamber is adjusted to be a ground relative to the two voltages. In one aspect, the middle chamber comprises a medium for providing conductance between each of the pores and the electrode in the middle chamber. In one aspect, the middle chamber comprises a medium for providing a resistance between each of the pores and the electrode in the middle chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the upper chamber to the middle chamber and to the lower chamber, or the other way around, sequentially. In some aspects, when the two voltages are set to opposite polarity, a charged particle can be moved from either the upper or the lower chamber to the middle chamber and kept there.

The adjustment of the voltages in the device can be particularly useful for controlling the movement of a large molecule, such as a charged polymer, that is long enough to cross both pores at the same time. In such an aspect, the direction and the speed of the movement of the molecule can be controlled by the relative magnitude and polarity of the voltages as described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Figure 5B:
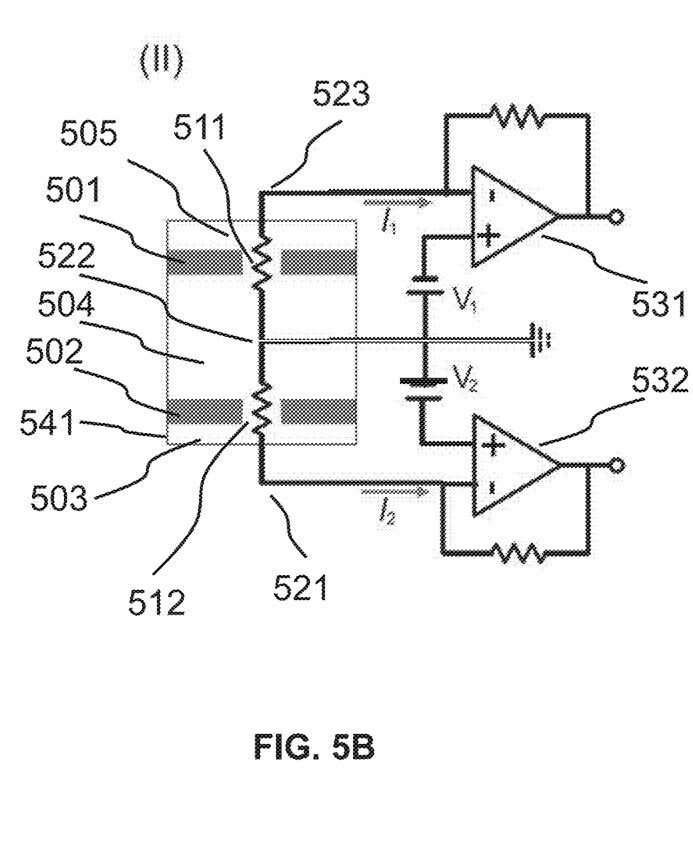
FIG. 5B is a schematic where electrically, $V_1$ and $V_2$ are principally applied across the resistance of each nanopore, by constructing a device that minimizes all access resistances to effectively decouple $I_1$ and $I_2$.

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C. In one aspect as shown in FIG. 5B, the housing would provide minimal access resistance between the voltage electrodes 521, 522, and 523 and the nanopores 511 and 512, to ensure that each voltage is applied principally across each pore.

In one aspect, the device includes a microfluidic chip (labeled as "Dual-core chip") comprising two parallel membranes connected by spacers. Each membrane contains a pore drilled by a single beam through the center of the membrane. Further, the device preferably has a Teflon® housing for the chip. The housing ensures sealed separation of Chambers A-C and provides minimal access resistance for the electrode to ensure that each voltage is applied principally across each pore.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath that comprises the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

In another aspect, the insertion of biological nanopores into solid-state nanopores to form a hybrid pore can be used in either or both pores in the two-pore method. The biological pore can increase the sensitivity of the ionic current measurements, and is useful when only single-stranded polynucleotides are to be captured and controlled in the two-pore device, e.g., for sequencing.

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber.

One example concerns a charged polymer scaffold, such as a DNA, having a length that is longer than the combined distance that includes the depth of both pores plus the distance between the two pores. For example, a 1000 bp dsDNA is about 340 nm in length, and would be substantially longer than the 40 nm spanned by two 10 nm-deep pores separated by 20 nm. In a first step, the polynucleotide is loaded into either the upper or the lower chamber. By virtue of its negative charge under a physiological condition at a pH of about 7.4, the polynucleotide can be moved across a pore on which a voltage is applied. Therefore, in a second step, two voltages, in the same polarity and at the same or similar magnitudes, are applied to the pores to move the polynucleotide across both pores sequentially.

Figure 5C:
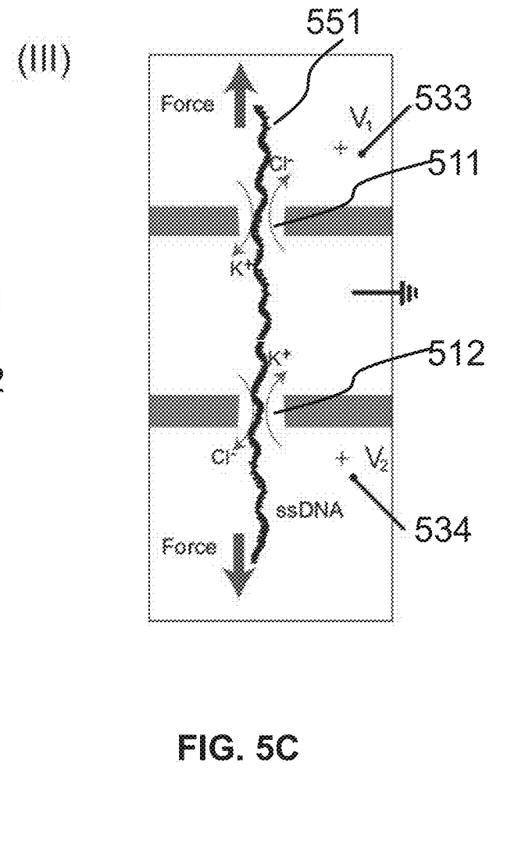
In FIG. 5C, competing voltages are used for control, with arrows showing the direction of each voltage force.

At about time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of polarity of the voltage at the first pore, therefore, will generate a force that pulls the polynucleotide away from the second pore as illustrated in FIG. 5C.

Assuming that the two pores have identical voltage-force influence and $|V_1|=|V_2|+\delta V$, the value $\delta V>0$ (or $<0$) can be adjusted for tunable motion in the $V_1$ (or $V_2$) direction. In practice, although the voltage-induced force at each pore will not be identical with $V_1=V_2$, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications.

Accordingly, in one aspect, provided is a method for controlling the movement of a charged polymer through a nanopore device. The method entails (a) loading a sample comprising a charged polymer in one of the upper chamber, middle chamber or lower chamber of the device of any of the above embodiments, wherein the device is connected to power supplies for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber (voltage-competition mode), wherein the two voltages are different in magnitude, under controlled conditions, so that the charged polymer moves across both pores in either direction and in a controlled manner.

To establish the voltage-competition mode in step (c), the relative force exerted by each voltage at each pore is to be determined for each two-pore device used, and this can be done with calibration experiments by observing the influence of different voltage values on the motion of the polynucleotide, which can be measured by sensing known-location and detectable features in the polynucleotide, with examples of such features detailed later in this disclosure. If the forces are equivalent at each common voltage, for example, then using the same voltage value at each pore (with common polarity in upper and lower chambers relative to grounded middle chamber) creates a zero net motion in the absence of thermal agitation (the presence and influence of Brownian motion is discussed below). If the forces are not equivalent at each common voltage, achieving equal forces involves the identification and use of a larger voltage at the pore that experiences a weaker force at the common voltage. Calibration for voltage-competition mode can be done for each two-pore device, and for specific charged polymers or molecules whose features influence the force when passing through each pore.

In one aspect, the sample containing the charged polymer is loaded into the upper chamber and the initial first voltage is set to pull the charged polymer from the upper chamber to the middle chamber and the initial second voltage is set to pull the polymer from the middle chamber to the lower chamber. Likewise, the sample can be initially loaded into the lower chamber, and the charged polymer can be pulled to the middle and the upper chambers.

In another aspect, the sample containing the charged polymer is loaded into the middle chamber; the initial first voltage is set to pull the charged polymer from the middle chamber to the upper chamber; and the initial second voltage is set to pull the charged polymer from the middle chamber to the lower chamber.

In one aspect, the adjusted first voltage and second voltage at step (c) are about 10 times to about 10,000 times as high, in magnitude, as the difference between the two voltages. For instance, the two voltages can be 90 mV and 100 mV, respectively. The magnitude of the two voltages, about 100 mV, is about 10 times of the difference between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 6000 times, 8000 times or 9000 times as high as the difference between them. In some aspects, the magnitude of the voltages is no more than about 10000 times, 9000 times, 8000 times, 6000 times, 6000 times, 5000 times, 4000 times, 3000 times, 2000 times, 1000 times, 500 times, 400 times, 300 times, 200 times, or 100 times as high as the difference between them.

In one aspect, real-time or on-line adjustments to the first voltage and the second voltage at step (c) are performed by active control or feedback control using dedicated hardware and software, at clock rates up to hundreds of megahertz. Automated control of the first or second or both voltages is based on feedback of the first or second or both ionic current measurements.

Sensors

In one aspect, the nanopore device further includes one or more sensors to carry out the identification of the binding status of the binding motifs.

The sensors used in the device can be any sensor suitable for identifying a molecule or particle, such as a polymer. For instance, a sensor can be configured to identify the polymer by measuring a current, a voltage, a pH value, an optical feature, or residence time associated with the polymer or one or more individual components of the polymer. In one aspect, the sensor includes a pair of electrodes placed at two sides of a pore to measure an ionic current across the pore when a molecule or particle, in particular a polymer, moves through the pore.

In one embodiment, the sensor measures an optical feature of the polymer or a component (or unit) of the polymer. One example of such measurement includes the identification of an absorption band unique to a particular unit by infrared (or ultraviolet) spectroscopy.

When residence time measurements are used, the size of the unit can be correlated to the specific unit based on the length of time it takes to pass through the sensing device.

Still further, the sensor can include an enzyme distal to that sensor, which enzyme is capable of separating the terminal unit of the polymer from the penultimate unit thereby providing for a single molecular unit of the polymer. The single molecule, such as a single nucleotide or an amino acid, can then be detected with methods such as mass spectrometry. Methods for measuring such a single unit are known in the art and include those developed by Cal Tech (see, e.g., spectrum.ieee.org/tech-talk/at-work/test-and-measurement/a-scale-for-weighing-single-molecules). The results of such analysis can be compared to those of the sensing device to confirm the correctness of the analysis.

In some embodiments, the sensor is functionalized with reagents that form distinct non-covalent bonds with each DNA base. In this respect, a gap formed by the sensor can be larger and still allow effective measuring. For instance, when used with a sensor functionalized with reagents, a 2.5 nm gap can be as effective as a 0.8 nm gap.

Tunnel sensing with a functionalized sensor is termed "recognition tunneling." Using a Scanning Tunneling Microscope (STM) with recognition tunneling, a DNA base flanked by other bases in a short DNA oligomer can be identified. Recognition tunneling can also provide a "universal reader" designed to hydrogen-bond to each of the four DNA bases (A, C, G, T) in a unique orientation, and also to the base 5-methyl-cytosine (mC) which is naturally occurring due to epigenetic modifications.

A limitation with the conventional recognition tunneling is that it can detect only freely diffusing DNA that randomly binds in the gap, or that happens to be in the gap during microscope motion, with no method of explicit capture to the gap. However, the collective drawbacks of the STM setup can be eliminated when the recognition reagent, once optimized for sensitivity, is incorporated within an electrode tunneling gap in a nanopore channel.

Accordingly, in one embodiment, the sensor comprises surface modification by a reagent. In one aspect, the reagent is capable of forming a non-covalent bond with a nucleotide. In a particular aspect, the bond is a hydrogen bond. Non-limiting examples of the reagent include 4-mercaptobenzamide and 1-H-lmidazole-2-carboxamide.

A significant advantage of the methods in the present technology is that they can be engineered, in principle, to provide direct tracking of progress through homopolymeric regions (base repeats). Tracking repeats is useful, for example, since deletions and insertions of specific mononucleotide repeats (7, 9 nt) within human mitochondrial DNA have been implicated in several types of cancer. Direct base repeat tracking is difficult, if not impossible, with ionic current sensing.

In ionic current sensing, there is no distinct signal-per-nucleotide of motion of homopolymeric ssDNA through the pore. Therefore, an ideal nanopore sequencing platform may include an auxiliary sensing method that can track per-nucleotide motion progress while also achieving single-nucleotide sensitivity. Transitions between neighboring nucleotides in oligomers can be observable with recognition tunneling, making it a candidate for sequencing that permits direct base-repeat tracking.

Therefore, the methods of the present disclosure can provide DNA delivery rate control for one or more recognition tunneling sites, each positioned in one or both of the nanopore channels, and voltage control can ensure that each nucleotide resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can sequence the translocating DNA.

In some embodiments, the tunnel gap has a width from about 1 nm to about 20 nm. In one aspect, the width of the gap is at least about 1 nm, or alternatively, at least about 1.5, 2, 2.5, 3, 3.5, 4, 4.5, 5, 6, 7, 8, 9, 10, 12, or 15 nm. In another aspect, the width of the gap is not greater than about 20 nm, or alternatively, not greater than about 19, 18, 17, 16, 15, 14, 13, 12, 11, 10, 9, 8, 7, 6, 5, 4, 3, or 2 nm. In some aspects, the width is between about 1 nm and about 15 nm, between about 1 nm and about 10 nm, between about 2 nm and about 10 nm, between about 2.5 nm and about 10 nm, or between about 2.5 nm and about 5 nm.

In some embodiments, the sensor is an electric sensor. In some embodiments, the sensor detects a fluorescent detection means when the target molecule or the detectable label passing through has a unique fluorescent signature. A radiation source at the outlet of the pore can be used to detect that signature.

It is to be understood that while the invention has been described in conjunction with the above embodiments, the foregoing description and examples are intended to illustrate and not limit the scope of the invention. Other aspects, advantages and modifications within the scope of the invention will be apparent to those skilled in the art to which the invention pertains.

The invention claimed is:

1. A method for detecting a target molecule or particle suspected to be present in a sample, comprising:
   (a) contacting the sample with (i) a fusion molecule comprising a ligand capable of binding to the target molecule or particle and a binding domain, and (ii) a polymer scaffold comprising a polymer and at least one binding motif to which the binding domain is capable of binding, under conditions that allow the target molecule or particle to bind to the ligand and the binding domain to bind to the binding motif;
   (b) loading the polymer scaffold into a device comprising a pore that separates an interior space of the device into two volumes, and
   (c) passing the polymer scaffold bound to a fusion molecule through the pore from one volume to the other volume, wherein the device further comprises a sensor adjacent to the pore capable of detecting objects passing through the pore; and
   (d) determining, with the sensor, whether the polymer scaffold bound to a fusion molecule is bound to the target molecule or particle, thereby detecting the presence of the target molecule or particle in the sample.

2. The method of claim 1, wherein the target molecule is selected from the group consisting of a protein, a peptide, a nucleic acid, a chemical compound, an ion, and an element.

3. The method of claim 1, wherein the target particle is selected from the group consisting of a protein complex or aggregate, a protein/nucleic acid complex, a fragmented or fully assembled virus, a bacterium, a cell, and a cellular aggregate.

4. The method of claim 1, wherein step (a) is performed prior to step (b).

5. The method of claim 1, wherein step (b) is performed prior to step (a).

6. The method of claim 1, further comprising applying a condition suspected to alter the binding between the target molecule or particle and the ligand, and carrying out the determination again.

7. The method of claim 6, wherein the condition is selected from the group consisting of removing the target molecule or particle from the sample, adding an agent that competes with the target molecule or particle, or the ligand for binding, and changing the pH, salt, or temperature.

8. The method of claim 1, wherein the binding motif comprises a chemical modification for binding to the binding domain.

9. The method of claim 8, wherein the chemical modification is selected from the group consisting of acetylation, methylation, SUMOylation, glycosylation, phosphorylation and oxidation.

10. The method of claim 1, wherein the polymer is at least one of a deoxyribonucleic acid (DNA), a ribonucleic acid (RNA), a peptide nucleic acid (PNA), a DNA/RNA hybrid, and a polypeptide.

11. The method of claim 1, wherein the binding domain is selected from the group consisting of a helix-turn-helix, a zinc finger, a leucine zipper, a winged helix, a winged helix turn helix, a helix-loop-helix, and a high mobility group box (HMG-box).

12. The method of claim 1, wherein the binding domain is selected from the group consisting of locked nucleic acids (LNAs), peptide nucleic acids (PNAs), transcription activator-like effector nucleases (TALENs), clustered regularly interspaced short palindromic repeats (CRISPRs), and aptamers.

13. The method of claim 1, wherein the ligand is selected from the group consisting of an antibody, an epitope, a hormone, a neurotransmitter, a cytokine, a growth factor, a cell recognition molecule, and a receptor.

14. The method of claim 1, wherein the binding domain and the ligand are linked, via a covalent bond, a hydrogen bond, an ionic bond, a metallic bond, a van der Waals force, a hydrophobic interaction, or a planar stacking interaction, or are translated as a continuous polypeptide, to form the fusion molecule.

15. The method of claim 1, further comprising contacting the sample with a detectable label capable of binding to the target molecule or particle, or the target molecule or particle/ligand complex.

16. The method of claim 1, wherein the polymer comprises at least two units of the binding motif.

17. The method of claim 1, wherein the polymer comprises at least two different binding motifs; the sample is in contact with at least two fusion molecules each comprising a different binding domain capable of binding to each binding motif and a different ligand capable of binding to a different target molecule or particle; and the sensor is capable of detecting whether the fusion molecule bound to each binding motif is bound to a target molecule or particle.

18. The method of claim 1, wherein the sensor comprises electrodes to apply a voltage differential between the two volumes.

19. The method of claim 1, wherein the device comprises an upper chamber, a middle chamber and a lower chamber,
   wherein the upper chamber is in communication with the middle chamber through a first pore, and the middle chamber is in communication with the lower chamber through a second pore;
   wherein the first pore and second pore are about 1 nm to about 100 nm in diameter, and are about 10 nm to about 1000 nm apart from each other; and
   wherein each of the chambers comprises an electrode connected to a power supply.

20. The method of claim 1, wherein the device comprises an upper chamber, a middle chamber and a lower chamber,
   wherein the upper chamber is in communication with the middle chamber through a first pore, and the middle chamber is in communication with the lower chamber through a second pore;
   wherein the first pore and second pore are about 100 nm to about 10000 nm in diameter, and are about 10 nm to about 1000 nm apart from each other; and
   wherein each of the chambers comprises an electrode for connecting to a power supply.

21. The method of claim 1, further comprising moving the polymer in a reversed direction after the binding motif passes through the pore to detect, again, whether the fusion molecule bound to each binding motif is bound to a target molecule or particle.

\* \* \* \* \*